United States Patent [19]

Igaue et al.

[11] Patent Number: 4,743,241
[45] Date of Patent: May 10, 1988

[54] DISPOSABLE ABSORBENT UNDERPANTS

[75] Inventors: Takamitsu Igaue, Kawanoe; Kohji Inoue, Ehime, both of Japan

[73] Assignee: Uni-Charm Corporation, Ehime, Japan

[21] Appl. No.: 38,143

[22] Filed: Apr. 14, 1987

[30] Foreign Application Priority Data

Apr. 15, 1986 [JP] Japan .................................. 61-87590
Apr. 15, 1986 [JP] Japan .................................. 61-87591

[51] Int. Cl.⁴ .............................................. A61F 13/16
[52] U.S. Cl. ................................................ 604/385 A
[58] Field of Search .................. 604/385.1, 385.2, 394, 604/396, 358

[56] References Cited

U.S. PATENT DOCUMENTS 4,352,355 10/1982 Mesek et al. ...................... 604/385.2
4,610,681 9/1986 Strohbeen et al. .................. 604/396
4,641,381 2/1987 Heran et al. ....................... 604/385.2

Primary Examiner—John D. Yasko
Attorney, Agent, or Firm—Fred Philpitt

[57] ABSTRACT

Disposable absorbent underpants useful as training pants for babies, underpants for incontinents and the like, including a main body of underpants comprising a water-permeable topsheet destined to be in contact with wearer's skin, water-impermeable backsheet located on a side opposite to the topsheet and an absorbent core sandwiched between these two sheets, and elastic members adapted to form elastic gathers in a waist band and a pair of leg-holes, respectively.

11 Claims, 3 Drawing Sheets

DISPOSABLE ABSORBENT UNDERPANTS

BACKGROUND OF THE INVENTION

The present invention relates to disposable absorbent underpants and more particularly to such underpants provided in the form of completely assembled underpants to be used, for example, as training pants for babies or underpants for incontinents.

The disposable absorbent underpants provided in the form of completely assembled underpants and containing elastic members in the waist band and a pair of leg-holes, respectively, has already been disclosed by Japanese Unexamined Patent Publication No. 58-11507. The underpants constructed in accordance with this prior art comprise the laterally elongate rectangular water-permeable topsheet dimensioned to form the front and rear areas, the water-impermeable backsheet identical to said topsheet both in the shape and the dimension, the absorbent cores sandwiched between these sheets leaving the central area defined midway between the laterally opposite ends of said sheets as the blank space so as to associate the respective absorbent cores with the front and rear areas, the elastic member adhesively fixed onto the backsheet along the upper end thereof so as to associate this elastic member with the waist band and the elastic member similarly fixed onto the backsheet along the lower end thereof so as to associate the elastic member with the respective leg-holes. The main body of underpants thus constructed is folded back along the central line of said blank area, then the front and rear area are joined together along the side edges thereof which are opposite to said blank area and finally the front and rear area are joined along the lower end of the central area defined between said side edges and the other side edge formed by folding back said blank area to form completely assembled underpants The underpants of said prior art is certainly advantageous in that the manufacturing thereof is simplified but involve various inconveniences such that the function of absorption is inadequate since the components of the front and rear areas to be joined together are concentrated in the crotch area; these components are disjoined or broken, resulting in loss of the desired function as the underpants and leakage of excretions since the crotch area is subjected to the highest tensile force due to movement of the wearer's legs; and said components give the wearer feelings of uncomfortable incompatibility. In addition, the front and rear areas are identically dimensioned, so that the area corresponding to hip is placed under a tension (i.e., becomes "tight") while the area corresponding to belly slackens (i.e., becomes "loose") due to rigidity of the components of underpants, particularly of the absorbent cores and the figure of human body (baby).

Furthermore, with the underpants of said prior art, said elastic members are sandwiched between said topsheet and said backsheet as extending substantially over the width of said cores or slightly beyond the length thereof, so said elastic members, particularly those associated with said respective leg-holes which are important to prevent excretions from leakage around the crotch hardly have their portions being capable of elastically functioning without any adverse influence of the rigidity inherent in said cores and, with a consequence, a sealing effect of said leg-holes is unsufficient to avoid leakage of excretions. Additionally, when said joining is effected by welding, the portions thus joined together will become stiffer relative to the remaining portions and give the wearer pain or even injury as a result of contact of said joined portions with the wearer's skin, since no particular care is not paid for such manner of joining.

Moreover, as the underpants in which the waist band portions associated with the front and rear areas, respectively, are connected into the annular band, it is impossible to adjust an overlapping width of the laterally opposite sides of the front and rear areas and a tightness of the area adjacent and inclusive of the waist band, this being possible with the disposable diaper of open type in which said waist band portions are connected by tape fastener in actual use of the diaper. As a further inconvenience, wrinkles due to slackening are formed in the area adjacent the lower edge of the waist band in the front area when the underpants are actually worn, since the components of the underpants are more rigid than those of the fabric diaper and baby's belly generally projects forwards.

The object of the present invention is, therefore, to provide improved disposable absorbent underpants adapted to overcome the drawbacks as have been set forth hereinabove by most simple measures.

ASPECT OF THE INVENTION

Said object is achieved, in accordance with the present invention, by providing disposable absorbent underpants including a main body of underpants comprising a water-permeable topsheet destined to be in contact with wearer's skin, a water-impermeable backsheet located on a side opposite to the topsheet and an absorbent core sandwiched between these two sheets, and elastic members adapted to form elastic gathers in a waist band and a pair of leg-holes, respectively, wherein said pair of leg-holes are defined by corresponding cutaway areas formed in laterally opposite sides of a crotch area as viewed in a developed condition of said main body; wherein said elastic members associated with said pair of leg-holes surround the corresponding cutaway areas except the outer edges thereof as viewed in the developed condition of said main body; and wherein said main body is assembled by folding said main body along a mid-line dividing said main body into vertically contiguous two halves back onto itself and then joining these two halves folded back onto each other along laterally opposite side edges of the folded main body.

The underpants constructed in the form of completely assembled underpants according to the present invention can achieve improvement not only in its appearance when actually worn but also in its fitness around the body of the wearer, and, therefore, are suitable particularly as training pants for babies and underpants for incontinents or demented olds.

One of the most important features of the underpants constructed in accordance with the present invention lies in that the cutaway areas defining the respective leg-holes are formed in the laterally opposite sides of the crotch area as viewed in the developed condition of the underpants and said leg-holes are incorporated with the associated elastic members so that the respective leg-holes are surrounded by the associated elastic members when the underpants have been completely assembled. Such a feature assures that said leg-holes perfectly fit around the legs and block any leakage of excretions therearound.

In a preferred embodiment of the present invention, the elastic members associated with the leg-holes extend outwards a predetermined length beyond the opposite side edges of the core which is more rigid than the topsheet and the backsheet due to its component material and its thickness. As a result, these extensions of the elastic members can provide their inherent elasticity substantially free from an adverse influence of the rigid core, assuring that the sealing effect of said leg-holes around the wearer's legs is improved and block further effectively leakage of excretions across such area.

The lines along which the front and rear areas are welded together are defined by grooves and edges extending outside these lines are left not joined. Thus, portions hardened as a result of the welding are not directly in contact with the wearer's skin and it is effectively refuced that these portions would otherwise give the wearer pain or injury. Further important features of the present invention such that the rear area is dimensioned larger than the front area, said cutaway areas defining said leg-holes are offset towards said front area with respect to the vertically mid-line and there are provided in opposite side edges as viewed in the developed condition of the underpants, in order to improve a fitness around the body, notches functioning as tucks which are, in turn, joined together along their side edges well contribute to resolution of the problem encountered by the conventional underpants of this type, i.e., the problem such that the area corresponding to the wearer's hip is subjected to a tension while the area corresponding to the wearer's belly slackens due to the rigidity of the components and the figure of the wearer. In this manner, said fitness is still further improved.

Lateral widths of the respective lower portions of the front and rear areas ar dimensioned larger than those of the respective waist band portions and the rear area itself is dimensioned larger than the front area in consideration of the feature that the cutaway areas defining the respective leg-holes formed in the laterally opposite sides of the crotch area as viewed in the developed condition of the underpants are offset towards the front area. In this way, once the underpants have been worn, the underpants can maintain a good fitness around the body without inconveniences that the area corresponding to the wearer's belly becomes tight, wrinkles due to slack occur in the area adjacent the lower portion of the waist band in the front area and the underpants as a whole slip down, even though the wearer's belly projects forwards as unexceptionally seen in the case of baby and the main body of the underpants consists of relatively rigid components.

Finally, the elastic members respectively associated with the waist band portions and the leg-holes are disposed substantially in parallel to one another and, therefore, easily incorporated into the associated components or the underpants, optically for mass production of the underpants at a low cost.

PREFERRED EMBODIMENTS OF THE INVENTION

Figure 1:
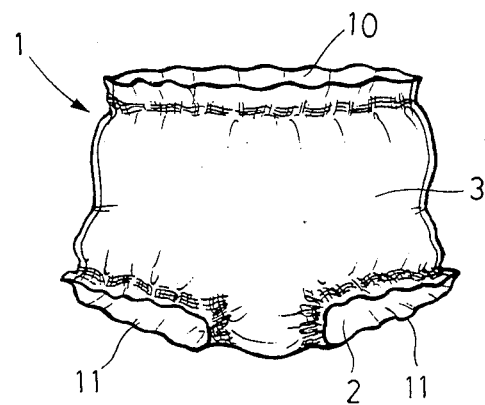
FIG. 1 is a perspective view showing an embodiment of the underpants constructed in accordance with the present invention.
Figure 2:
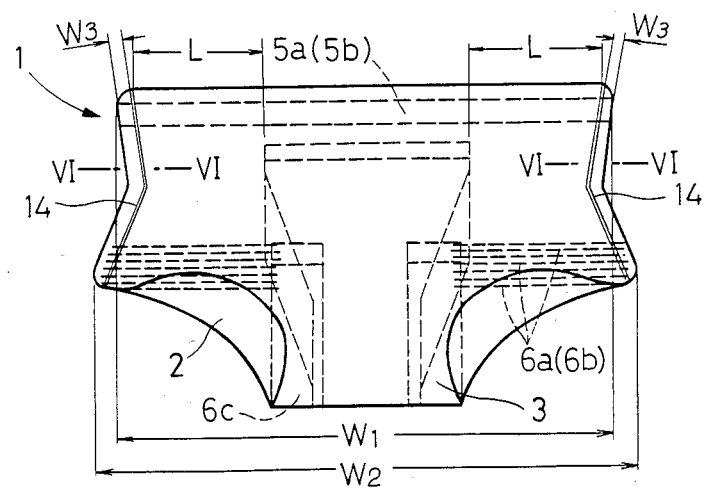
FIG. 2 is a front view showing said underpants as have been assembled.
Figure 3:
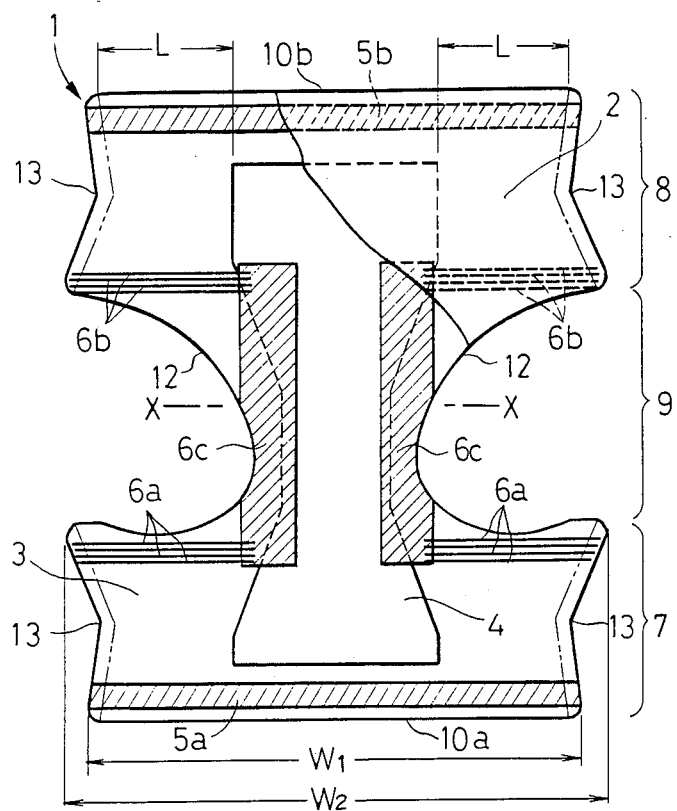
FIG. 3 is a plan view showing the underpants of FIG. 2 as developed.

Referring to FIGS. 1 through 3, a main body 1 of underpants includes a water-permeable topsheet 2, a water-impermeable backsheet 3 being identical to said topsheet in its dimension and an absorbent core 4 smaller than these two sheets. The main body 1 further includes elastic members 5a, 5b destined to form elastic gathers in associated waist band portions which define together, in turn, a waist band 10, and elastic members 6a, 6b, 6c destined to form elastic gathers in leg-holes 11.

The topsheet 2 is made of nonwoven fabric containing therein at least thermal-weldable fibres, the backsheet 3 is made of plastic film o laminate sheet of said film and nonwoven fabric, and the core 4 consists of fluffy pulp or a mat of mixture of said pulp and highly absorptive polymer particles and water-permeable sheets (not shown) disposed on upper and lower surfaces thereof. The elastic members 5a, 5b, 6c are made of urethane foam or plastic film exhibiting elasticity upon heat treatment which are relatively wide, e.g., 10 to 45 mm while the elastic members 6a, 6b comprise a plurality of rubber strings. Along vertically opposite ends of the topsheet 2 as well as the backsheet 3 in a front area 7 and a rear area 8 of the underpants before assembled or folded back, i.e., along respective waist lines 10a, 10b, the elastic members 5a, 5b are sandwiched between the topsheet 2 and the backsheet 3. The elastic members 5a, 5b, 6a, 6b, particularly the elastic members 6a, 6b preferably extend outwards beyond respective side edges of the core 4 in the front area 7 and the rear area 8 by 10 to 130 mm, more preferably by 30 to 110 mm, most preferably by 50 to 95 mm. This length is indicated by L which corresponds to a distance from the respective side edges of the core 4 to respective inner side edges of grooves 14 along which welding is effected. These grooves 14 will be described later.

In a crotch area 9, the topsheet 2 and the backsheet 3 are provided in laterally opposite sides thereof with semielliptic cutaway areas 12 which are offset towards the front area 8 with respect to a vertically mid-line X of the main body 1 of underpants to define respective leg-holes 11. Thus the rear area 8 is dimensioned larger than the front area 7 in the main body 1. The front area 7 and the rear area 8 are incorporated adjacent vertically opposite ends of the respective cutaway areas 12 with the elastic members 6a, 6b extending substantially in parallel to said elastic members 5a, 5b and adjacent laterally opposite side edges of the pair of said cutaway areas 12 with the elastic members 6c extending substantially transverse of the horizontal and connected with the associated elastic members 6a, 6b. These elastic members surround the associated cutaway areas 12. Of course, it is also possible to dispose a single elastic member in a curve extending along the contour of the associated cutaway area 12. However, the arrangement as shown is advantageous over such single elastic member arrangement, since operation of adhesively fixing the respectively elastic members in a process of manufacturing is drastically simplified and thus high speed production is achieved. The front area 7 and the rear area 8 are provided along their laterally opposite side edges large-angled V-shape notches 13 functioning as tucks to improve fitness. The core 4 is adhesively fixed between the topsheet 2 and the backsheet 3 in a relatively stationary manner so that said core 4 occupies a central zone of the sheets with a narrow width in the crotch area 9 and has a larger dimension in the rear area 8 than in the front area 8. Adhesively joining together of the topsheet 2 and the backsheet 3 along their outer peripheries, adhesively fixing the elastic members 5a, 5b, 6b, 6c onto the topsheet 2 and/or the backsheet 3, and adhesively fixing of the core 4 onto the topsheet 2 and/or the backsheet 3 are effected by adhesive of hot melt type or thermal welding.

A lateral width $W_2$ of the front area 7 and the rear area 8 along their lower ends is larger than a lateral width $W_1$ of the front area 7 and the rear area 8 along their waist band portions 10a, 10b.

Figure 4:
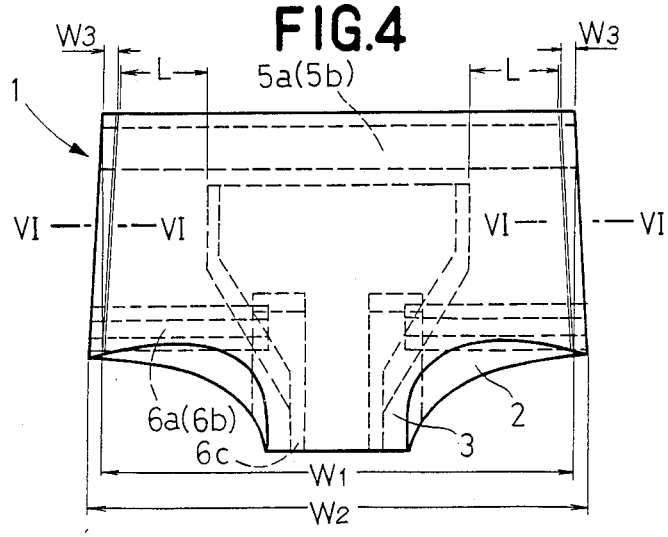
FIG. 4 is a front view showing another embodiment of the present invention as have been assembled.
Figure 5:
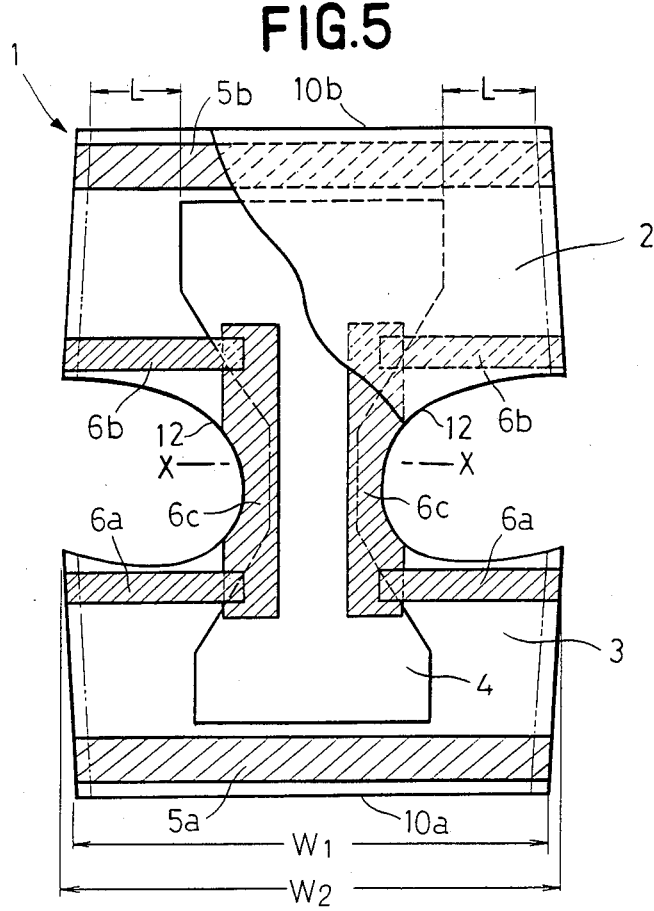
FIG. 5 is a plan view showing the underpants of FIG. 4 as developed.
Figure 6:
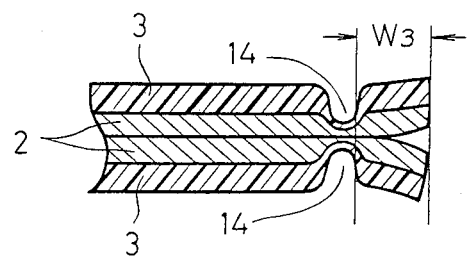
FIG. 6 is an enlarged section taken along line VI—VI in FIGS. 2 and 4.

Referring to FIGS. 4 and 5, another embodiment of the main body 1 is illustrated. This main body 1 is substantially same as that of said previously mentioned embodiment except that the front area 7 as well as the rear area 8 are gradually narrower from the crotch area 9 to the respective waist band portions 10a, 10b. The elastic members 6a, 6b are made of relatively wide urethane foam or plastic film exhibiting elasticity upon heat treatment.

As seen in FIGS. 1, 2 and 4, the main body 1 is folded back along the mid-line X (see FIGS. 3 and 5) in the vertical direction with the topsheet 2 being located inside and welded under a pressure in continuous line along opposite side edges of the front area 7 and the rear area 9, leaving the outer-most edges of a suitable width $W_3$, preferably less than 10 mm not welded. In this case, in order to improve a weldability and therefore a weld strength, it is preferred to interpose plastic film having its melting point lower than these of both the topsheet 2 and the backsheet 3 along the lines of welding between the topsheet 2 and the backsheet 3 or between the surfaces of the same topsheet 3 to be in contact with each other.

What is claimed is:

1. Disposable absorbent underpants including a main body of underpants comprising a water-permeable topsheet destined to be in contact with wearer's skin, a water-impermeable backsheet located on a side opposite to the topsheet and an absorbent core sandwiched between these two sheets, and elastic members adapted to form elastic gathers in a waist band and a pair of leg-holes, respectively, wherein said pair of leg-holes are defined by corresponding cutaway areas formed in laterally opposite sides of a crotch area as viewed in a developed condition of said main body; wherein said elastic members associated with said leg-holes surround the corresponding cutaway areas except the outer edges thereof as viewed in the developed condition of said main body; and wherein said main body is assembled by folding said main body along a mid-line dividing said main body into vertically contiguous two halves back onto itself and then joining these two halves folded back onto each other along laterally opposite side edges of the folded main body.

2. Underpants as defined by claim 1, wherein the elastic members associated with said leg-holes comprise, as viewed in the developed condition of said main body, first members laterally extending along vertically opposite ends of said cutaway areas and second members vertically extending along laterally opposite edges of said cutaway areas and connected with said first members.

3. Underpants as defined by claim 1, wherein, of said elastic members, at least the first members associated with said leg-holes extend outwards beyond the respective outer edges of said core by 10 to 130 mm.

4. Underpants as defined by claim 1, wherein joining of said main body is effected by welding said main body with said topsheet inside along the laterally opposite edges thereof so that said welding is performed along lines defined by grooves and the outer-most edges wide less than 10 mm of said main body are left not welded.

5. Underpants as defined by claim 1, wherein a lateral width of said front area and said rear area as measured along their lower ends is larger than that of said waist band portions in said front area and said rear area.

6. Underpants as defined by claim 1, wherein the cutaway areas defining said leg-holes are, as viewed in the developed condition of said main body, offset towards said front area with respect to said mid-line.

7. Underpants as defined by claim 1, wherein said rear area is larger than said front area as viewed in the developed condition of said main body.

8. Underpants as defined by claim 1, wherein said main body includes notches functioning as tucks along laterally opposite side edges and between vertically opposite ends in the respective areas.

9. Underpants as defined by claim 1, wherein both said front area and said rear area are configured to be gradually tapered from said cutaway areas defining said leg-holes towards the waist band portions therein, respectively.

10. Underpants as defined by claim 1, wherein the elastic members associated with said waist band portions extend substantially in parallel to the respective first members of said elastic members laterally extending along the vertically opposite ends of the respective cutaway areas defining said leg-holes as viewed in the developed condition of said main body.

11. Underpants as defined by claim 1, wherein the respective second members of the elastic members vertically extending along the laterally opposite side edges of the respective cutaway areas defining said leg-holes are substantially in parallel to one another as viewed in the developed condition of said main body.

* * * * *